United States Patent [19]

Sime et al.

[11] 4,303,656

[45] Dec. 1, 1981

[54] AMINOMETHYL CHROMANS

[75] Inventors: John T. Sime, Ewell; Anthony T. Ainsworth, Cranleigh, both of England

[73] Assignee: Beecham Group Limited, England

[21] Appl. No.: 145,856

[22] Filed: May 1, 1980

[30] Foreign Application Priority Data

May 19, 1979 [GB] United Kingdom ............... 17495/79

[51] Int. Cl.$^3$ ................... A61K 31/35; C07D 311/58; C07D 413/00; C07D 405/06
[52] U.S. Cl. .............................. 424/248.4; 260/345.2; 544/151; 546/196; 424/248.53; 424/248.54; 424/248.55; 424/248.56; 424/267; 424/283; 424/248.57
[58] Field of Search ...................... 260/345.2; 546/196; 544/151; 424/283, 248.4, 248.53, 248.54, 248.55, 248.56, 248.57, 267

[56] References Cited

U.S. PATENT DOCUMENTS 4,146,539  3/1979  Gardner .............................. 546/196
4,234,726  11/1980  Gardner .............................. 544/151

*Primary Examiner*—Nicky Chan
*Attorney, Agent, or Firm*—Jacobs & Jacobs

[57] ABSTRACT

A compound of the general formula (III), having anorexic activity:

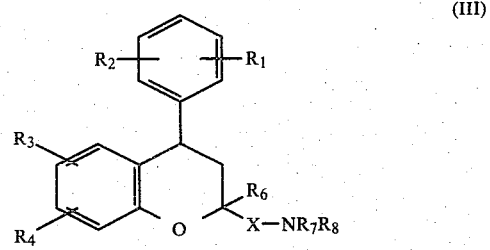

(III)

or a salt thereof, wherein $R_1$, $R_2$, $R_3$ and $R_4$ may be the same or different and are each a hydrogen or halogen atom, or a trifluoromethyl, $C_1$ to $C_4$ alkyl, $C_1$ to $C_4$ alkoxy, hydroxyl, carboxyl, $C_1$ to $C_4$ alkoxycarbonyl, amino or acetamido group; $R_6$ is a hydrogen atom or a $C_1$ to $C_4$ alkyl group; X is a straight or branched alkylene group of up to 4 carbon atoms; and $R_7$ and $R_8$ which may be the same or different are each a hydrogen atom or a $C_1$ to $C_4$ alkyl group, or $R_7$ is joined to $R_8$ so that $NR_7R_8$ forms a 5–7 membered heterocyclic ring.

11 Claims, No Drawings

AMINOMETHYL CHROMANS

This invention relates to novel chroman derivatives having anorexic activity, to pharmaceutical compositions containing them, and to processes for their preparation.

U.S. Pat. No. 3,743,659 discloses 1-phenylisochroman derivatives of the formula (I):

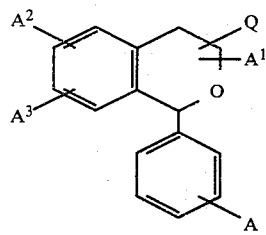

wherein A is hydrogen, lower alkyl, halogen, trifluoromethyl, amino, N-lower alkylamino or N,N-di-lower alkylamino; $A^1$ is hydrogen or lower alkyl, $A^2$ and $A^3$ are each hydrogen, lower alkyl, lower alkoxy, hydroxy, halogen or trifluoromethyl and Q is a radical attached to either the 3 or 4 position, having the structure.

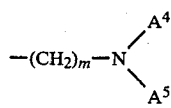

wherein $A^4$ and $A^5$ are independently hydrogen, lower alkyl or hydroxy-lower alkyl or, when taken together with the nitrogen atom to which they are attached, form a 5 - or 6-membered nitrogen-containing ring having from 3 to 5 carbon atoms in the ring, one of which may be replaced by an oxygen atom, m is zero to 4 and when m is 1 or more, the alkylene chain may contain a substituent methyl group; and salts thereof. These compounds are said to be CNS-active agents, having anticonvulsant, depressant and anorexic activity.

U.S. Pat. No. 3,851,062 discloses 1-phenylisochromans of the formula (II):

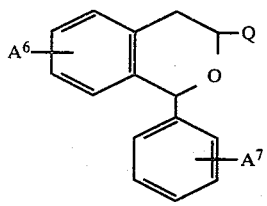

wherein $A^6$ is hydrogen, fluorine or chlorine in the 6- or 7-position; $A^7$ is hydrogen, fluorine, chlorine or trifluoromethyl; and Q is 2-imidazolinyl or $(CH_2)_nNA^8A^9$ wherein $A^8$ and $A^9$ are hydrogen or lower alkyl, and n is 0, 1 or 2 with the $(CH_2)_n$ alkylene chain optionally substituted by methyl. These compounds are said to be anorexigenic without causing CNS stimulation.

We have now discovered that certain derivatives of 2-aminoalkyl-4-phenylchromans have particularly good anorexic activity.

Accordingly, this invention provides the compounds of the formula (III):

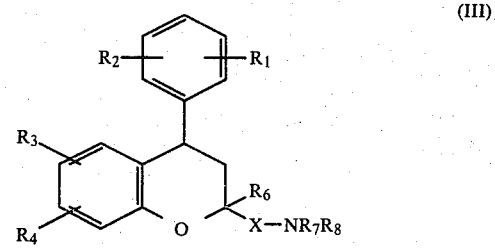

and salts thereof, wherein $R_1$, $R_2$, $R_3$ and $R_4$ may be the same or different and are each a hydrogen or halogen atom, or a trifluoromethyl, $C_1$ to $C_4$ alkyl, $C_1$ to $C_4$ alkoxy, hydroxyl, carboxyl, $C_1$ to $C_4$ alkoxycarbonyl, amino or acetamido group; $R_6$ is a hydrogen atom or a $C_1$ to $C_4$ alkyl group; X is a straight or branched alkylene group of up to 4 carbon atoms; and $R_7$ and $R_8$ which may be the same or different are each a hydrogen atom or a $C_1$ to $C_4$ alkyl group, or $R_7$ is joined to $R_8$ so that $NR_7R_8$ forms a 5–7 membered heterocyclic ring.

When used herein, the term "halogen" means fluorine, chlorine or bromine.

Suitably $R_2$ is a hydrogen atom.
Suitably $R_4$ is a hydrogen atom.
Preferably $R_2$ and $R_4$ are both hydrogen atoms.
Suitably X is a $CH_2$ or $CH(CH_3)$ group.
Suitably $R_1$ is a hydrogen or chlorine atom or a trifluoromethyl, $C_1$ to $C_4$ alkyl or $C_1$ to $C_4$ alkoxy group.
Suitably $R_3$ is a hydrogen or chlorine atom or a trifluoromethyl, $C_1$ to $C_4$ alkyl or $C_1$ to $C_4$ alkoxy group.
Suitably $R_6$ is a hydrogen atom or a methyl group.
Suitably $R_7$ and $R_8$ are each a hydrogen atom or a methyl group, or are linked to form part of a piperidino or morpholino group.
Preferably, $R_7$ and $R_8$ are hydrogen atoms or methyl groups.
Preferably, $R_1$ is a hydrogen or chlorine atom.
Preferably, $R_3$ is a hydrogen or chlorine atom.

When the 4-phenyl group in the compounds of the formula (III) is substituted, it is preferred that one of the substituents is in the 4'-position.

Thus it will be realised that preferred compounds of this invention include those of the formula (IV):

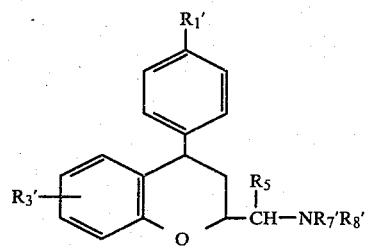

and salts thereof, wherein $R'_1$ and $R'_3$ are independently a hydrogen or chlorine atom, $R'_7$ and $R'_8$ are independently a hydrogen atom or a methyl group, and $R_5$ is a hydrogen atom or a methyl group.

Particularly preferred compounds of this invention are the compounds of the formula (IV) wherein $R'_1$ is a chlorine atom and $R'_3$ is a hydrogen atom and acid addition salts thereof.

Suitable acids which may be used to form acid addition salts of the compounds of the formula (III) are pharmaceutically acceptable acids, for example, those of inorganic and organic acids, such as hydrochloric, phosphoric, sulphuric, methanesulphonic, toluenesulphonic, citric, malic, acetic, lactic, tartaric, propionic, succinic, hydrobromic or the like acid.

The compounds of this invention have anorexic activity, so that in a further aspect, this invention provides a pharmaceutical composition comprising a compound of the formula (III) or a salt thereof and a pharmaceutically acceptable carrier.

Such compositions are useful for inducing anorexia.

The compositions may contain diluents, binders, fillers, disintegrants, flavouring agents, colouring agents, lubricants, preservatives or the like in accordance with conventional pharmaceutical practice.

Preferably, the compositions of this invention will be in unit dose form adapted for oral administration. Unit dose compositions will normally comprise from 0.05–100 mg of active compound, more usually from 0.25–50 mg of active compound.

The normal daily dose for an adult human will be from 0.2–200 mg per day, more usually from 1–100 per day, administered as 1–4, more usually 3–4 doses.

This invention further provides a process for the preparation of the compounds of the formula (III), which process comprises the reduction of a compound of the formula (V):

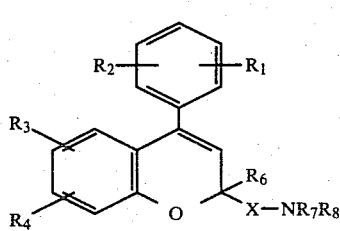

(V)

or a salt thereof, wherein $R_1$, $R_2$, $R_3$, $R_4$, $R_6$, $R_7$, $R_8$ and X are as defined in relation to formula (III).

The reduction may be effected by hydrogenation in an inert solvent in the presence of a transition metal catalyst. A low, medium or high pressure of hydrogen may be used, but in general, it is preferred to use an atmospheric or slightly super-atmospheric pressure of hydrogen. Suitably catalysts include platinum, palladium and the like, for example, Adams catalyst or palladium on charcoal. Suitable solvents include water, lower alcohols, tetrahydrofuran, dioxane and acetic acid or mixtures of such solvents.

Compounds of the formula (V) and salts thereof may be prepared by the dehydration of a corresponding compound of the formula (VI):

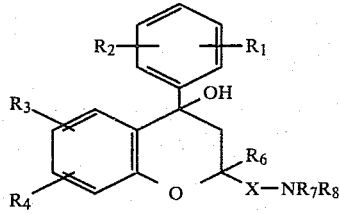

(VI)

or a salt thereof.

The reaction may occur spontaneously or on heating the compound in an inert solvent, preferably in the presence of an acid catalyst.

The compounds of the formulae (V) and (VI) are novel, and form an aspect of this invention.

Compounds of the formula (III) may also be prepared by the catalytic hydrogenation of a compound of the formula (VII):

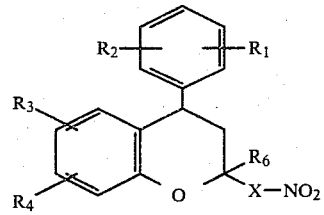

(VII)

wherein $R_1$, $R_2$, $R_3$, $R_4$, $R_6$ and X are as defined in relation to formula (III) and thereafter, if desired, alkylating the resulting compound of the formula (III) wherein $R_7$ and $R_8$ are both hydrogen atoms to produce a compound of the formula (III) wherein at least one of $R_7$ and $R_8$ is not a hydrogen atom.

Compounds of the formula (VII) may be prepared by the reaction of nitromethane or nitroethane with the corresponding compound of the formula (VIII):

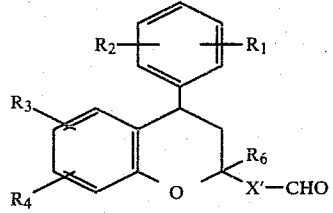

(VIII)

wherein X' is a bond or a $CH_2$ or $CH_2$—$CH_2$ group or such a group substituted by a methyl group, followed by reduction of the resulting 2-(nitroalkenyl)-chroman. Normally, the reduction of the alkenyl group and of the nitro group are effected simultaneously, although the alkenyl group may be reduced before the nitro group, if desired. Compounds of the formula (VII) wherein X is a $CH_2$ or $CH(CH_3)$ group may also be prepared by the reaction of nitromethane or nitroethane with a compound of the formula (IX):

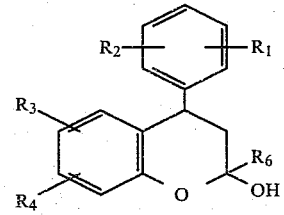

(IX)

in the presence of a tertiary amine.

Compounds of the formula (III) may also be prepared by the reduction of a compound of the formula (X):

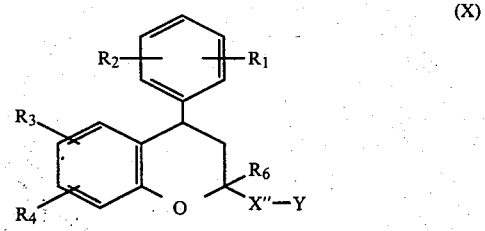

wherein X" is a group such that X"—CH₂ is a group X and Y is a CN or CO.NR₇R₈ group, and thereafter, if desired, alkylating the resulting compound of the formula (III) when at least one of R₇ and R₈ is a hydrogen atom to produce a compound of the formula (III) wherein at least one of R₇ and R₈ is not a hydrogen atom.

The reduction may be effected by conventional methods, for example, using a complex metal hydride when Y is CN or a CO.NR₇R₈ group, or by catalytic hydrogenation when Y is a CN group.

Compounds of the formula (VI) may be prepared by the reaction of a compound of the formula (XI):

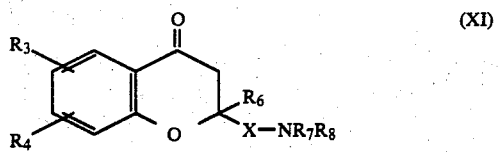

wherein X, R₃, R₄, R₆, R₇ and R₈ are as defined in relation to formula (III) with a compound of the formula (XII):

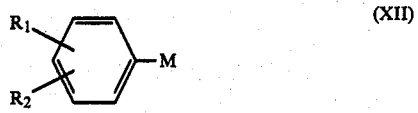

wherein R₁ and R₂ are as defined in relation to formula (III) and M is an alkali metal or MgZ where Z is a halogen.

Suitable compounds (XII) include those wherein M is lithium.

This reaction will be carried out in conditions conventionally used for Grignard reactions.

Compounds of the formula (XI) may be prepared by the reaction of an appropriately substituted amino-aldehyde amino ketone or an acetal thereof with an appropriately substituted 2-hydroxyacetophenone.

Compounds of the formula (XI) wherein R₆ is hydrogen may also be prepared by the reduction of a compound of the formula (XIII):

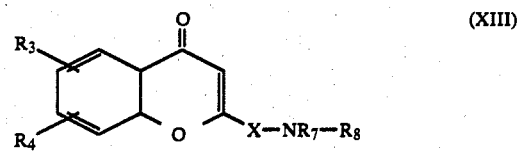

wherein X, R₃, R₄, R₇ and R₈ are as defined in relation to formula (XI).

Suitably, the reduction is effected using lithium aluminum hydride at a depressed temperature, for example, abut −80° C. The solvent used will be one conventionally used in lithium aluminum hydride reductions, such as an ether, for example diethyl ether or tetrahydrofuran.

Compounds of the formula (XIII) may be prepared by the reaction of an appropriately substituted 2-hydroxyacetophenone with an ester of an amino-substituted carboxylic acid.

Compounds of the formula (III) wherein one or both of R₇ and R₈ is a hydrogen atom may be prepared by the catalytic hydrogenation of a corresponding compound wherein one or both of R₇ and R₈ is a benzyl group.

The reaction conditions will be conventional, for example, using a low, medium or high pressure of hydrogen, in the presence of a catalyst such as palladium on carbon, in an inert solvent.

Acid addition salts of compounds of the formula (III) may be prepared in conventional manner, for example, by the reaction of an acid with a compound of the formula (III).

The following Examples illustrate the invention:

EXAMPLE 1

2-(N,N-dimethylaminomethyl)-4-(4'-chlorophenyl)-chroman (a) 2-(N,N-dimethylaminomethyl)chroman-4-one Dimethylaminoacetaldehyde diethyl acetal (40 g) was treated below −5° C. with conc. hydrochloric acid (196 ml) and then stirred at room temperature for 2 hours. After the solution had been neutralised with sodium bicarbonate, 2 N sodium hydroxide (80 ml) was added followed by 2-hydroxyacetophenone (34 g) in 2 N sodium hydroxide (80 ml) and sufficient dioxane to give a single phase reaction mixture. The solution was heated at 70°–80° C. with stirring for 2½ hours and left at ambient temperature overnight.

Extraction with diethyl ether was followed by extraction of the organic phase with dilute hydrochloric acid. The aqueous acid solution was basified with sodium hydroxide solution and extracted into diethyl ether to give the title compound (3.4 g) as an oil.

$^1H$ nmr (CDCl₃) δ: 8.1−6.9 (m, 4H); 4.9−4.4 (m, 1H); 3.0−2.5 (m, 4H); 2.3 (s, 6H).

The compound was further characterised as the hydrochloride salt mp 222°–224° C. ex ethanol crystallising as the monohydrate.

(b) 2-(N,N-dimethylaminomethyl)-4-hydroxy-4-(4'-chlorophenyl)-chroman.

To a solution of 4-bromochlorobenzene (1.87 g) in dry diethyl ether (20 ml) at −78° C. was added butyl lithium in hexane (1.6 M, 6.2 ml) under dry nitrogen and the solution then allowed to warm to room temperature.

The chromanone produced in (a) above (2 g) in diethyl ether (15 ml) was added slowly with stirring and then boiled under refluxed for 1½ hours. The reaction mixture was cooled, poured on to ice/dilute hydrochloric acid and the acidic solution washed with diethyl ether. The aqueous phase was basified with sodium hydroxide solution and extracted with diethyl ether. The ethereal extracts were dried (MgSO₄) and evaporated to give the title compound (1.45 g) as an oil.

$^1H$ nmr (CDCl₃) δ: 7.5−6.6 (m), 7.2 (s), (8H); 4.3 (broad m, 1H) 4.2 (m, 1H); 2.8−2.1 (m), 2.1 (s), 2.2 (s), (10H).

(c) 2-(N,N-dimethylaminomethyl)-4-(4-chlorophenyl)-3-chromene

A solution of 2-(N,N-dimethylaminomethyl)-4-hydroxy-4 (4'-chlorophenyl)-chroman (1.35 g) and tosic acid (10 mg) in benzene (75 ml) was heated under reflux with azeotropic removal of water for 3½ hours. The solvent was removed under reduced pressure, the residue taken up in diethyl ether and washed with 2 N sodium hydroxide (20 ml). The organic phase was dried (MgSO₄) and evaporated to give the title compound (1.08 g) as an oil.

$^1$H nmr (CDCl$_3$) δ: 2.3 (s, 6H); 2.5—2.8 (m, 3H); 5.0 (m, 1H); 5.7 (d, 1H); 6.7–7.5 (m, 4H); 7.2 (s, 4H).

(d)  2-(N,N-Dimethylaminomethyl)-4-(4'-chlorophenyl)chroman 2-(N,N-Dimethylaminomethyl)-4-(4'-chlorophenyl)-3-chromene (0.36 g) and Adams catalyst (PtO$_2$) (5 mg) in ethanol (30 ml) was hydrogenated at atmospheric pressure. When hydrogen uptake was complete (4 hours) the catalyst was removed by filtration and the solution evaporated to give an oil which was chromatographed on alumina using chloroform as eluant. The eluate was evaporated to give, after trituration with petroleum ether (40°/60°) the title compound (200 mg) as a white solid, mp 120°–122° C.

EXAMPLE 2

2-Dimethylaminomethyl-4-phenylchroman hydrobromide

The process of Example 1 was repeated, using phenyl lithium in place of the 4-bromochlorobenzene/butyl lithium in part (b), to yield the title compound, mp 219°–222° C.

EXAMPLE 3

6-Chloro-2-dimethylaminomethyl-4-phenylchroman

The process of Example 1 was repeated, using 5-chloro-2-hydroxyacetophenone in place of the 2-hydroxyacetophenone in part (a) to yield the title compound.

$^1$H nmr (CDCl$_3$) δ: 1.8–2.9 (m), 2.35 (s) (10H); 3.9–4.5 (m, 2H); 6.7–7.5 (m, 8H).

EXAMPLE 4

2-(1-N,N-Dimethylaminoethyl)-4-(4-chlorophenyl)-chroman (a) 2-(1-N,N-Dimethylaminoethyl)-chromone To a suspension of sodium hydride (11.9 g) in absolute dioxane (200 ml), stirred at 80° C., was slowly added a mixture of o-hydroxyacetophenone (22.6 g) and N,N-dimethylalanine ethyl ester (24.5 g) in dioxane (50 ml), and the resulting solution was boiled for 3 hours before being evaporated in vacuo. The residue was digested in ethanol and the mixture was saturated with dry HCl and stirred at room temperature for 18 hours. After evaporation the residue was taken up in chloroform and washed with dilute sodium hydroxide solution. Evaporation of the dried organic extracts yielded the product as an oil (20.5 g).

$^1$H nmr (CDCl$_3$) δ: 1.45 (d, 3H); 2.32 (s,6H); 3.42 (q, 1H); 6.27 (s, 1H); 7.20–8.30 (m, 4H).

(b) 2-(1-N,N-Dimethylaminoethyl)-chroman-4-one

A stirred solution of 2-(1-N,N-dimethylaminoethyl)-chromone (10 g) in dry THF (400 ml) at −78° C., was treated with a suspension of LiAlH$_4$ (2.7 g) in dry THF (100 ml) and the resulting mixture was stirred at −78° C. for 4 hours before being acidified with glacial acetic acid and filtered. The filtrate was evaporated, basified with 2 N NaOH solution and extracted with chloroform. The washed dried organic extracts were evaporated to yield the product (7.8 g) as a liquid.

$^1$H nmr (CDCl$_3$) δ: 1.13 (d, 3H); 2.25 (s, 6H); 2.5–3.2 (m, 3H); 4.4 (m, 1H); 6.7–8.0 (m, 4H).

(c)  2-(1-N,N-dimethylaminoethyl)-4-(4-chlorophenyl)-4-hydroxychroman

To an ice cooled solution of 4-bromochlorobenzene (9.95 g) in dry diethyl ether (100 ml) was added butyl lithium in hexane (1.6 M, 32.5 ml) under dry nitrogen and the solution was allowed to reach room temperature.

2-(1-N,N-dimethylaminoethyl)-chroman-4-one (5.7 g) in diethyl ether (30 ml) was added slowly with stirring and then boiled under reflux for 1½ hours. The reaction mixture was cooled, poured onto ice/dilute hydrochloric acid and the acidic solution was washed with diethyl ether. The aqueous phase was basified with sodium hydroxide solution and extracted with diethyl ether. The dried ethereal extracts were evaporated to give the title compound as an oil (5.0 g).

$^1$H nmr (CDCl$_3$) δ: 1.08 (d, 3H); 2.1–3.0 (m, 9H); 3.5 (m, 1H); 4.15 (m, 1H); 6.6–7.6 (m, 8H).

(d)  2-(1-N,N-Dimethylaminoethyl)-4-(4-chlorophenyl)-3-chromene 2-(1-N,N-dimethylaminoethyl)-4-(4-chlorophenyl)-4-hydroxychroman (5.9 g) was stirred at room temperature in 5 N hydrochloric acid (50 ml) for 18 hours. The reaction mixture was basified with sodium hydroxide solution and extracted with chloroform to yield the title compound as an oil, (5.0 g).

$^1$H nmr (CDCL$_3$) δ: 1.13 (d, 3H); 2.30 (s, 6H); 2.8 (m, 1H); 4.85 (m, 1H); 5.82 (d, 1H); 6.7–7.5 (m, 8H).

(e)  2-(1-N,N-Dimethylaminoethyl)-4-(4-chlorophenyl)chroman 2-(1-N,N-dimethylaminoethyl)-4-(4-chlorophenyl)-3-chromene (2.5 g) and Adam's catalyst (PtO$_2$) (30 mg) in ethanol (100 ml) was hydrogenated at atmospheric pressure. When hydrogen uptake was complete the catalyst was removed by filtration and the solution was evaporated. The resulting oil was chromatographed on alumina eluting with chloroform. The eluate was evaporated to give the title compound (1.4 g) as a white solid. mp 128°–129° C. (petrol bp 40°–60° C.).

EXAMPLE 5

2-Aminomethyl-4-Phenylchroman 2-(N,N-Dibenzylaminomethyl)-4-phenyl-3-chromene

The process of Example 4 was repeated using N,N-dibenzylglycine ethyl ester in place of N,N-dimethylalanine ethyl ester in part (a), then following the precedure in part (b) and in part (c) using phenyl lithium in place of the 4-bromochlorobenzene/butyl lithium, to yield the title compound as an oil, after dehydration in dilute HCl as in part (d).

$^1$H nmr (CDCl$_3$) δ: 2.9 (m, 2H); 3.70 (s, 4H); 5.1 (m, 1H); 5.61 (d, 1H); 6.7–7.7 (m, 19H).

2-Aminomethyl-4-phenylchroman 2-(N,N-dibenzylaminomethyl)-4-phenyl-3-chromene (2.2 g) was hydrogenated at 651b in $^{-2}$ in glacial acetic acid in the presence of 5% palladium on carbon (15 mg) until no more hydrogen was taken up. After filtration and removal of solvent in vacuo the residue was treated with ethereal HBr and the resulting solid recrystallised from ethanol/ether to give the title compound as the hydrobromide salt (0.9 g), mp 243°–245° C.

EXAMPLE 6

2-(1-N,N-Dimethylaminoethyl)-4-[4-(trifluoromethyl)-phenyl]chroman

The process of example 4 was repeated using 4-bromobenzotrifluoride in place of the 4-bromochlorobenzene in part (c) to yield the title compound, m.p. 106°–108° C.

EXAMPLE 7

2-(2-N,N-Dimethylaminoethyl)-4-(4-chlorophenyl)-chroman

The process of example 4 was repeated using ethyl 3-N,N-dimethylaminopropionate in place of N,N-dimethylalanine ethyl ester in part (a) to yield the title compound $^1$H n.m.r. (CDCl$_3$) δ: 1.6–2.9 (m. 12H); 3.8–4.4 (m. 2H); 6.5–7.4 (m. 8H).

EXAMPLE 8

2-N,N-Dimethylaminomethyl)-4-(3-chlorophenyl)chroman

The process of example 4 was repeated using N,N-dimethylglycine ethyl ester in place of N,N-dimethylalanine ester in part (a), and using 3-bromochlorobenzene in place of 4-bromochlorobenzene in part (c) to yield the title compound which was isolated as the hydrobromide salt.

m.p. 205°–206° C.

EXAMPLE 9

2-(N,N-Dimethylaminomethyl)-4-[4-(trifluoromethyl)-phenyl]chroman

The process of example 4 was repeated using N,N-dimethylglycine ethyl ester in place of N,N-dimethylalanine ethyl ester in part (a), and using 4-bromobenzotrifluoride in place of 4-bromochlorobenzene in part (c) to yield the title compound.

$^1$Hnmr (CDCl$_3$) δ: 1.7–2.9 (m. 10H); 4.0–4.5 (m. 2H); 6.5–7.7 (m. 8H).

EXAMPLE 10

2-(N,N-Dimethylaminomethyl)-4-(4-methylphenyl)-chroman

The process of example 4 was repeated using N,N-dimethylglycine ethyl ester in place of the N,N-dimethylalanine ethyl ester in part (a), and using 4-bromotoluene in place of the 4-bromochlorobenzene in part (c) to yield the title compound, m.p. 114°–116° C.

EXAMPLE 11

2-(N,N-Dimethylaminomethyl)-4-(4-chlorophenyl)-6-fluorochroman

The process of example 4 was repeated using N,N-dimethylglycine ethyl ester in place of the N,N-dimethylalanine ethyl ester and using 5-fluoro-2-hydroxyacetophenone in place of the o-hydroxyacetophenone in part (a) to yield the title compound which was isolated as the hydrobromide salt, m.p. 154°–156° C.

EXAMPLE 12

2-(N,N-dimethylaminomethyl)-2-methyl-4-(4-chlorophenyl)chroman (a) 2-(N,N-dimethylaminomethyl)-2-methylchroman-4-one o-Hydroxyacetophenone (11.42 g) was added to a solution of lithium diisopropylamide (0.167 moles) in tetrahydrofuran (100 ml) at −25° C. under an atmosphere of dry nitrogen and the resulting solution was stirred at this temperature for 1 hour after which the temperature was lowered to −40° C. and (dimethylamino) acetone (8.49 g) was slowly added. The mixture was stirred for 1.5 hours at −40° C. before being acidified with dilute hydrochloric acid then neutralized with sodium bicarbonate.

Ether extraction of the solution gave an oil which was boiled under reflux, for 2 hours in a 10% solution of concentrated hydrochloric acid in methanol (100 ml) before being evaporated, diluted with water, and basified, after which, extraction gave an oil which was purified by chromatography on alumina eluting with ether to give the title compound as an oil (2.4 g).

1H n.m.r. (CDCl$_3$) δ 1.36 (s, 3H); 2.33 (s, 6H); 2.36–3.28 (m, 4H); 6.78–7.89 (m, 4H).

(b) 2-(N,N-dimethylaminomethyl)-2-methyl-4-(4-chlorophenyl)chroman

The processes of example 1 parts (b), (c) and (d) were repeated to yield the title compound which was isolated as the hydrochloride salt.

m.p. 223°–225° C.

EXAMPLE 13

2-(1-aminoethyl)-4-phenylchroman (a) 2-(1-N,N-dibenzylaminoethyl)chroman-4-one

The process of example 4 was repeated using N,N-dibenzylalanine ethyl ester in place of N,N-dimethylalanine-ethyl ester in part (a). The title compound was isolated as an oil.

$^1$H n.m.r. (CDCl$_3$) δ 1.2–1.35 (m, 3H); 2.1–4.5 (m, 8H); 7.0–7.9 (m, 14H).

Mass. Spec. (ammonia chemical induction) M$^+$. 372 (P+H)$^+$; 288; 224; 91.

(b) 2-(1-aminoethyl)-4-phenylchroman

A stirred solution of 2-(1-N,N-dibenzylaminoethyl)-chroman-4-one in ether under an atmosphere of dry nitrogen, was treated at 0° C. with a four molar excess of phenyl lithium and the resulting solution was boiled under reflux for 5.5 hours before being cooled, poured onto ice/dilute hydrochloric acid and extracted with chloroform to give the crude 2-(1-N,N-dibenzylaminoethyl)-4-phenyl-4-hydroxychroman as an oil.

i.r. spectrum (liquid film), ν cm$^{-1}$; Broad signal around 3330 (OH); 1605 (M); 1584 (M); 1493 (S); 1480 (S); 1452 (S).

A solution of this hydroxychroman and tosic acid in benzene was heated to reflux with azeotropic removal of water for 18 hours before being treated with ethereal hydrogen chloride. The oil which separated was dissolved in chloroform and washed with 2 M. sodium hydroxide, then dried and evaporated, to give a crude mixture of chromenes as an oil.

$^1$H n.m.r. (CDCl$_3$) δ : 7.49–6.63 (m); 5.79 (d) and 5.60 (d) (1H); 4.93 (m, 1H); 4.09–3.0 (m); 1.30–1.12 (2×d, 3H).

i.r. spectrum (liquid film), ν cm$^{-1}$; 1602 (S); 1495 (S); 1485 (S); 1454 (S).

This oil and Adams catalyst (PtO$_2$) in glacial acetic acid was hydrogenated at atmospheric pressure. When hydrogen uptake was complete the catalyst was removed by filtration and the solution evaporated to give an oil which was dissolved in ether and washed with dilute sodium hydroxide solution, the resulting product being chromatographed on alumina using chloroform as eluant. The eluate was evaporated to yield the title compound which was isolated as the hydrobromide monohydrate.

m.p. 215°–220° C. (d).

EXAMPLE 14

2-(N,N-dimethylaminomethyl)-4-(4-chloro-3-trifluoromethylphenyl)chroman

The process of example 4 was repeated using N,N-dimethylglycine ethyl ester in place of N,N-dimethylalanine ethyl ester in part (a), and using 5-bromo-2-chlorobenzotrifluoride in place of 4-bromochlorobenzene in part (c) to yield the title compound which was isolated as the hydrochloride salt.

m.p. 223°–235° C. (sublimes at 193°–195° C.).

EXAMPLE 15

2-(N,N-dimethylaminomethyl)-4-(4-methoxyphenyl)-chroman

The process of example 4 was repeated using N,N-dimethylglycine ethyl ester in place of N,N-dimethylalanine ethyl ester in part (a), and using p-bromoanisole in place of 4-bromochlorobenzene in part (c) to yield the title compound which was isolated as the hydrobromide salt.

m.p. 226°–228° C.

EXAMPLE 16

2-(N-methylaminomethyl)-4-phenylchroman (a) 2-(N-benzyl-N-methylaminomethyl)chromone To a suspension of sodium hydride (16.4 g) in absolute dioxane (700 ml) stirred at 80° C., was slowly added a mixture of o-hydroxyacetophenone (31.0 g) and N-benzyl-N-methylglycine ethyl ester (40 g) in dioxane (100 ml), and the resulting solution was boiled for 19 hours before being evaporated in vacuo. The residue was dissolved in ethanol and the mixture was saturated with dry HCl and stirred at room temperature for 18 hours. After evaporation the residue was taken up in chloroform and washed with water. Evaporation of the dried organic extracts yielded an oil (40 g) which was chromatographed on alumina eluting with chloroform to give the title chromone as a yellow oil (17.8 g).

$^1$H n.m.r. (CDCl$_3$) δ 2.37 (s, 3H); 3.46 (s, 2H); 3.65 (s, 2H); 6.47 (s, 1H); 7.19–7.75 (m); 8.19 (d, 1H).

(b) 2-(N-benzyl-N-methylaminomethyl)chroman-4-one

A stirred solution of 2-(N-benzyl-N-methylaminomethyl)chromone (15.6 g) in dry tetrahydrofuran (400 ml) at −78° C., was treated with a suspension of LiAlH$_4$ (3.2 g) in dry tetrahydrofuran (50 ml) and the resulting mixture was stirred at −78° C. for 4 hours before being acidified with glacial acetic acid and allowed to stand at room temperature for 17 hours. The mixture was then filtered and the filtrate was evaporated, dissolved in chloroform and washed with water. The dried, evaporated organic extracts gave an oil which was chromatographed on alumina eluting with ether to give the title compound as a yellow oil (4.9 g).

$1_H$ n.m.r. (CDCl$_3$) δ : 2.37 (s, 3H); 2.67–2.81 (m, 4H); 3.60 (s, 2H); 4.54 (m, 1H); 6.86–7.51 (m); 7.83 (dd, 1H).

(c) 2-(N-benzyl-N-methylaminomethyl)-4-phenyl-3-chromene

To a stirred solution of 2-(N-benzyl-N-methylaminomethyl)chroman-4-one (4.9 g) in dry diethyl ether (200 ml) under an atmosphere of dry nitrogen at room temperature, was added a two molar excess of phenyllithium solution and the resulting mixture was boiled for 2 hours before being poured onto ice/dilute HCl. The solution was basified and extracted with ether to give the crude 2-(N-benzyl-N-methylaminomethyl)-4-phenyl-4-hydroxychroman as an orange oil.

i.r. spectrum (liquid film), ν cm$^{-1}$; Broad signal around 3320 (S); 1610 (M); 1584 (M); 1483 (S); 1454 (S).

A solution of this hydroxychroman and tosic acid in benzene was boiled with azeotropic removal of water for 18 hours before being washed with 2 N sodium hydroxide solution then water. The dried, evaporated organic extracts yielded an oil which was chromatographed on alumina, eluting with ether to yield the title chromene as an oil (4.9 g).

$^1$H n.m.r. (CDCl$_3$) δ : 2.33 (s, 3H); 2.48–2.86 (m, 2H); 3.60 (s, 2H); 5.05 (m, 1H); 5.70 (d, 1H); 6.70–7.64 (m).

(d) 2-(N-methylaminomethyl)-4-phenylchroman 2-(N-benzyl-N-methylaminomethyl)-4-phenyl-3-chromene (4.9 g) and 5% palladium on carbon in ethanol was hydrogenated at 65 lb in $^{-2}$ until hydrogen uptake was complete. After filtration and evaporation of solvent the residue was chromatographed on alumina eluting with chloroform to give a clear oil, which on treatment with ethereal hydrogen chloride yielded the title compound as the hydrochloride salt, (1.1 g).

m.p. 233°–235° C.

PHARMACOLOGICAL ACTIVITY

The compounds of the preceding examples were tested for anorexigenic activity by measuring the reduction in food intake by hungry rats following administration of the compound.

The results are shown below:

| Compound of example No. | Dose mg/kg p.o. | % Anorexia (4 hours) |
| --- | --- | --- |
| 1 | 16 | 50 |
| 2 | 50 | 38 |
| 3 | 50 | 23 |
| 4 | 2.5 | 56 |
| 5 | 50 | 90 |
| 6 | 15 | 86 |
| 7 | 50 | 20 |
| 8 | 50 | 64 |
| 9 | 50 | 36 |
| 10 | 50 | 41 |
| 11 | 50 | 66 |
| 12 | 20 | 50 |
| 13 | 20 | 21 |
| 14 | 20 | 29 |
| 15 | 50 | 51 |
| 16 | 20 | 39 |

We claim:

1. A compound selected from the group consisting of a chroman of the formula:

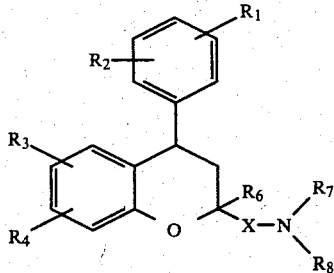

and the pharmaceutically acceptable acid addition salts thereof wherein each of $R_1$, $R_2$, $R_3$ and $R_4$, independently of the others is hydrogen, halo, trifluoromethyl, alkyl of 1 to 4 carbon atoms, alkoxy of 1 to 4 carbon atoms, hydroxy, carboxy, alkoxycarbonyl of 1 to 4 carbon atoms in the alkoxy group, amino or acetamido;

$R_6$ is hydrogen or alkyl of 1 to 4 carbon atoms;

X is straight or branched chain alkylene of up to 4 carbon atoms, and each of $R_7$ and $R_8$, when taken independently, is hydrogen or alkyl of 1 to 4 carbon atoms or $R_7$ and $R_8$ when taken together with the nitrogen atom to which they are attached, are piperidino or morpholino.

2. A compound according to claim 1, wherein $R_2$ is hydrogen.

3. A compound according to claim 1, wherein $R_4$ is hydrogen.

4. A compound according to claim 1, wherein $R_2$ and $R_4$ are both hydrogen.

5. A compound according to claim 4, wherein each of $R_1$ and $R_3$ is independently hydrogen, chloro, trifluoromethyl, alkyl or alkoxy.

6. A compound according to claim 5, wherein $R_6$ is hydrogen or methyl.

7. A compound according to claim 1, wherein $R_7$ and $R_8$ are independently hydrogen or methyl or together with the nitrogen to which they are attached piperidino or morpholino.

8. A compound according to claim 1, wherein $R_1$ is in the 4-position of the depicted phenyl ring and is hydrogen or chloro, $R_3$ is hydrogen or chloro, each of $R_2$, $R_4$ and $R_6$ is hydrogen, X is methylene or ethylidene and $R_7$ and $R_8$ are independently hydrogen or methyl.

9. A compound according to claim 8, wherein $R_1$ is chloro and $R_3$ is hydrogen.

10. A pharmaceutical composition comprising an anorexically effective amount of a compound according to claim 1 in combination with a pharmaceutical carrier.

11. The method of effecting an anorexic response in a human or other animal which comprises administering thereto an effective amount of a compound according to claim 1.

* * * * *